United States Patent [19]

Hydo

[11] 4,036,064
[45] July 19, 1977

[54] PIPETTE DEVICE

[75] Inventor: Steven J. Hydo, Wellington, Ohio

[73] Assignee: Gilford Instrument Laboratories, Inc., Oberlin, Ohio

[21] Appl. No.: 612,351

[22] Filed: Sept. 11, 1975

[51] Int. Cl.$^2$ .................................................. B01L 3/02
[52] U.S. Cl. ..................................................... 73/425.6
[58] Field of Search ........................... 73/425.4 P, 425.6

[56] References Cited

U.S. PATENT DOCUMENTS

| 3,410,664 | 11/1968 | Fielding | 73/425.6 |
| 3,646,817 | 3/1972 | Hinchman | 73/425.6 |

Primary Examiner—S. Clement Swisher
Attorney, Agent, or Firm—Baldwin, Egan, Walling & Fetzer

[57] ABSTRACT

A pipette device enabling single samples of fluids to be readily analyzed under emergency conditions "STAT," as for example, body fluids, and which device is operable to first draw a predetermined volume of a selected reagent material into its chamber, and thereafter in similar manner draw a desired volume of the sample fluid to be analyzed into said device, said reagent material and fluid thereafter being ejected into a suitable reaction vessel wherein the same are admixed preparatory to being analyzed.

33 Claims, 12 Drawing Figures

FIG.1

| LIQUID REAGENT | LIQUID REAGENT | SAMPLE FLUID TO BE TESTED | REAGENT PLUS SAMPLE FLUID |
|---|---|---|---|
| FIG. 2A. | FIG. 2B. | FIG. 2C. | FIG. 2D |

PIPETTE DEVICE

BACKGROUND OF THE INVENTION

At present, one of the problems occurring in many clinical laboratories is the difficulties encountered in handling single samples for analysis that may come in at odd hours for emergency work-ups, the so-called STAT. Under these circumstances there are generally no automatic analyzers available, and the analytical procedures are geared to essentially manual methods. For the analysis of enzymes, for example, this requires that a carefully metered amount of fluid sample be mixed with a larger but equally carefully metered amount of reagent before they are inserted into any analyzing equipment such as a spectrophotometer for qualitative and/or quantitative measurement. Enzymatic reagents are rather costly, and the common practice is to open only small vials of reagent suitable for single tests.

The pipette device of the present invention is especially designed to enable a single sample of fluid, as for example a body fluid, to be readily analyzed which analysis may occur under emergency or "STAT" conditions and wherein essentially manual methods of sampling analysis are necessary. The pipette device herein disclosed likewise offers a very convenient and simple device for carefully and efficiently metering out both the sample to be analyzed and the reagent material in one device, and which is operable to accurately control the amounts of said reagent and sample used in said device which therefore makes it difficult to make an error and likewise eliminates the need to use highly skilled help.

SUMMARY OF THE INVENTION

Several preferred embodiments of the pipette device of the present invention are herein disclosed, each of which employs the principle of fluid displacement to accommodate two fluids in the one device, i.e., the proposed fluid sample to be analyzed and the reagent material to be used therewith.

In one embodiment of pipette device a predetermined volume of reagent material is initially drawn through the probe tip or nozzle of the pipette and into the pipette chamber by the manual manipulation of a plunger assembly. A known volume of the reagent material is then ejected or displaced from the chamber out through its probe tip by a subsequent actuation of the plunger assembly, and thereafter an identical volume of the fluid sample to be analyzed is drawn into probe tip or nozzle of the pipette by a further actuation of the plunger assembly. Finally, the reagent material remaining in the pipette chamber and the fluid sample are expelled out through the probe tip by actuation of the plunger assembly and into a reaction vessel wherein they are admixed preparatory to being subjected to analysis.

In another embodiment of the present invention the pipette device is formed of coaxially arranged inner and outer barrel assemblies, the inner barrel assembly defining a plunger and piston unit for the outer barrel and being telescopically movable within the outer barrel to draw a predetermined volume of reagent material into the chamber of the outer barrel. The inner barrel assembly includes a plunger and piston unit which is thereafter movable within its associated inner barrel chamber to draw a prescribed volume of the reagent material from the outer barrel chamber into the inner chamber while simultaneously drawing a like volume of fluid sample to be analyzed into the probe tip or nozzle of the outer barrel. The outer barrel plunger assembly may then be depressed to eject the reagent material in the outer barrel chamber and the fluid sample into a reaction vessel wherein they are admixed. The plunder and piston unit of the inner barrel may then be depressed to force the reagent material in the inner barrel chamber out through the outer barrel chamber and probe tip sufficiently to rinse the same and prepare them for subsequent use.

In still another embodiment of pipette device of the present invention a displacement rod of exact dimensions attached to the movable plunger is projected into the primary fluid chamber to displace a like volume of reagent material therefrom. Thereafter, the rod is withdrawn out of said chamber as to aspirate or draw a like volume of fluid sample back into the probe tip or nozzle of the pipette. Thence, the plunger and piston unit is depressed sufficiently to expel the fluid sample and reagent material into a reaction vessel.

It is therefore a primary object of the invention to provide a pipette device relatively simple in construction and especially designed to operate on the principle of fluid displacement to carefully and efficiently meter predetermined volumes of fluid sample and reagent material in one device and which may be easily expelled into a reaction vessel preparatory to analysis.

Other objects of the pipette device of the present invention will become apparent to one skilled in the art to which it pertains, and upon reference to the following disclosure of several preferred embodiments thereof and which are illustrated in the accompanying drawings wherein:

FIGS. 2(A-D) are somewhat partially schematic sectional views of the pipette device of FIG. 1 illustrating the manner in which it is operable to aspirate and expel fluids into and from the same;

FIGS. 6(A-D) are partial sectional views of a third embodiments of pipette of the present invention illustrating the manner of its use.

Figure 1:
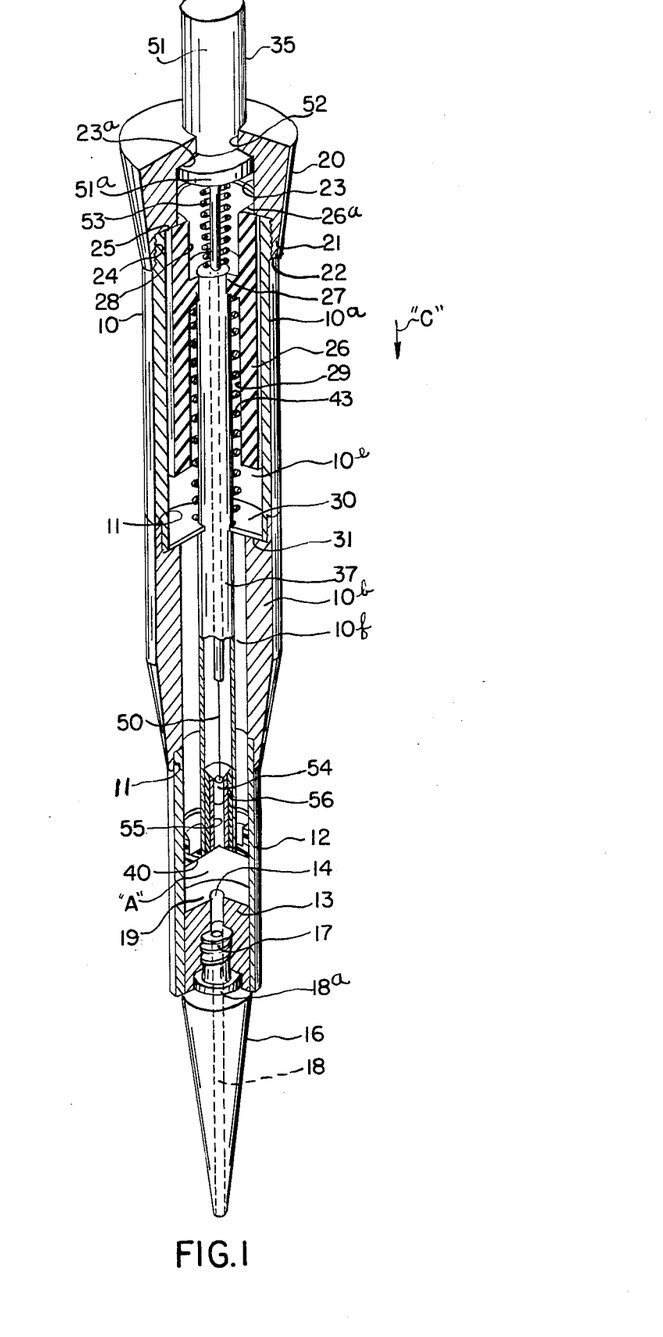
FIG. 1 is a longitudinal vertical sectional view of a first embodiment of the pipette device of the present invention and showing the same in its at rest condition.

With reference now directed to FIG. 1 the first embodiment of pipette device of the present invention is generally tubular in its overall design, having an elongated tubular body or shell 10 which may be formed of any suitable metal or nonmetallic material, as for example, aluminum or a suitable plastic material.

One end of the body 10 is provided with an annular seat 11 into which is securely fastened one end of tube 12, and which is preferably made of clear rigid glass or a suitable plactic material of like characteristics.

A plug 13 is disposed within the opposite end of tube 12 in fluid-tight relation, and is formed with a bore 14 extending centrally therethrough.

A probe tip or nozzle 16 is secured to the outward end of the plug 13 by any suitable means, such as by the threaded connection 17 and extends outwardly of the body 10. A suitable seal, as for example, 0-ring 18a may be interposed between the probe tip 16 and plug 13 to provide a liquid-tight seal therebetween. The probe tip 16 is provided with a central bore or passageway 18 extending longitudinally therethrough as shown, and which communicates with the bore 14 of plug 13. As seen in FIG. 1, the plug 13 extends into the tube 12 and terminates in a flat transverse wall or surface 19.

A cap 20 is attached to the opposite end of the body 10, being securely fastened thereto by any suitable means such as threaded connection 21. The cap 20 is formed with a central bore 22 of stepped configuration having an upper part 23 which is of lesser diameter than the lower part 24 to define an annular shoulder 25 therebetween. A sleeve member 26 formed by any suitable rigid material, as for example aluminum, is disposed within the upper end of the body 10 as viewed in FIG. 1, and as herein shown, is somewhat H-shaped in cross-section having a transverse wall 27 intermediate the ends thereof to define separate spring chambers 28 and 29. As will be hereinafter explained in greater detail, sleeve member 26 is slidably movable within the body 10 between a lower stop as defined in the present construction by flat washer 30 which seats upon annular shoulder 31 provided in said body 10 mediate its ends, and an upper stop defined by the annular shoulder 25 on cap 20.

A plunger and piston assembly as identified in its entirety at 35, is disposed within body 10 and actuatable to provide for the suction and expulsion of fluids therefrom.

For this purpose, this assembly 35 includes a tube member 37, which may be formed of metallic or nonmetallic material, and which has its one end extending centrally through the transverse wall 27 of the sleeve member 26 and is securely fastened thereto so as to be movable therewith, and to project centrally through the lower part of said sleeve member 27 as viewed in FIG. 1, the chamber 10e in upper shell part 10a, through the washer 30 and similarly into the chamber 10f in the lower shell part 10b.

A cylindrical piston 40 is attached to the opposite end of the tube member 37, and is preferably formed of a suitable material such as Teflon having a relatively low coefficient of friction. The diameter of piston 40 is such as to provide a slidable fluid-tight relationship between its wall and the internal surface of the tube 12.

With this construction a main fluid chamber A is thus provided in tube 12 between the piston 40 and plug 13.

The piston 40, attached tube 37 and sleeve member 26 are urged toward the cap member 20 by means of coil spring 43 surrounding tube 37 between the adjoining surfaces of the transverse wall 27 of sleeve member 26 and washer 30, the latter defining the lower stop for piston 40 travel.

As seen in FIG. 1, if force is then applied to sleeve member 26 in the direction of arrow C, said sleeve member 26, tube 37 and piston 40 will move downwardly within the shell 10, against the resistance of spring 43 until and bottom surface of sleeve member 26 strikes the flat wall 19 of plug 13 to define "zero volume" in chamber A whereby all fluid has been expelled from said chamber. This is the poition illustrated in FIG. 2D.

As aforementioned, the pipette of the present invention provides for the sequential introduction or aspiration into the pipette of an exact metered volume of reagent material, thence an exact metered volume of sample to be analyzed and thereafter for the expulsion of the reagent and sample into a suitable reaction vessel wherein they become admixed preparatory for analysis.

The accomplish the introduction of an exact metered volume of sample to be tested, the plunger and piston assembly 35 includes a secondary plunger assembly which comprises rod member 50 having its one end securely fastened to finger actuator button 51 which, in turn, is cylindrical in its present form, having an annular rim 51a at its one end. Actuator 51 projects through the bore 23 of cap 20, outwardly through a hole 52 formed in the top of the cap member 20 and is thus in position for manual actuation.

A coil spring 53 surrounding the rod member 50 and interposed between the top surface of the transverse wall 27 of the sleeve member 26, as seen in FIG. 1, and the actuator 51, normally urges said actuator and attached rod member 50 upwardly within the pipette body 10, the annular rim 51a of said actuator thus normally engaging the upper wall 23a of the cap bore 23 to thereby define the "at rest" position for said actuator 51. For reasons that will be hereinafter more fully apparent, the resistance to compression (modulus) of coil spring 53 is less than that of coil spring 43.

In the present embodiment, the rod member 50 has a piston 54 secured to its free end, and which is disposed within a cylindrical bore 55 formed in tube 56, said elements being formed to exact, precise dimensions. Tube 56 may be formed of any suitable material; however, the present material utilized in glass. Tube 56 is mounted within tube member 37, its lowermost end, as viewed in FIG. 1, being flush with the bottom surface of piston 40, the bore 55 thus communicating with the fluid chamber A.

And, as will be recalled, the modulus of coil spring 43 is selected as to be greater than the modulus of coil spring 53, or in other words, the resistance to compression of spring 43 is greater than that of spring 53.

Figure 2A:
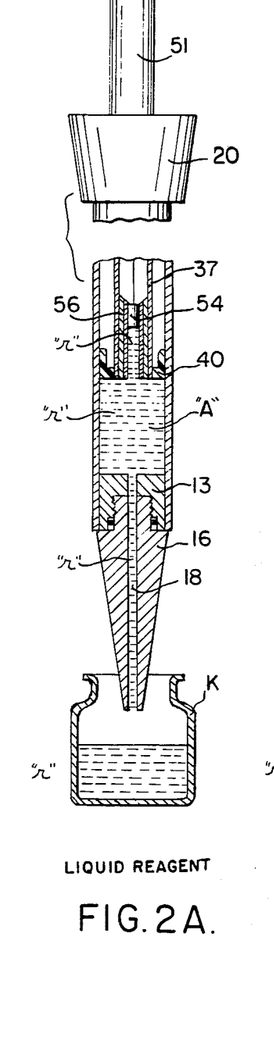
Figure 2B:
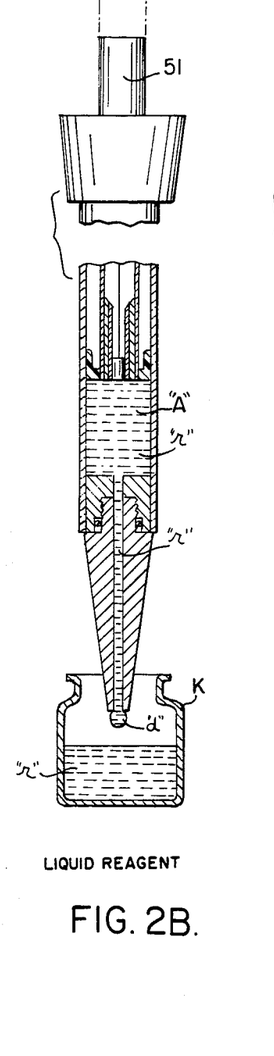

In its use, the pipette may be held in either hand with the thumb overlying the top of the actuator button 51, and upon initial pressure exerted by the thumb against the actuator button 51 in the direction of arrow C as viewed in FIG. 1, the rod member 50 and piston 54 are slidably moved against the pressure of coil spring 53 through tube member 37 and precision glass bore tube 56, respectively, until the annular rim 51a of the actuator button 51 engages the underlying top surface 26a of the sleeve member 26, said surface 26a thus defining the "lower stop" for piston 54 travel or stroke. This position for piston 54 is illustrated in FIG. 2B. In the present construction, the "lower stop" is engaged by the actuator button 51 at the same time the bottom face of the piston 54 is substantially aligned with the bottom edge of the glass bore tube 56. Also, as will be understood, this initial piston 54 travel or stroke may be varied by preselecting the distance between the rim 51a of the actuator and the top edge 26a of the sleeve member 26.

With the actuator buttom 51 engaging the sleeve member 26, continuation of thumb pressure sufficiently to overcome the resistance exerted by coil spring 43 will cause the sleeve 26 to be forced downwardly as viewed in FIG. 1 through the body chamber 10e, thereby causing piston 40 to be slidably moved downwardly through the main fluid chamber A. And, since said piston 40 is in fluid-tight relation with the internal surface of the tube 12, such movement therethrough will be effective to expel any air and/or fluid from said chamber A out through the communicating bore 14 in plug 13 and bore 18 in the probe tip to atmosphere. Continued depression of the actuator 51 may be permitted until the bottom edge of the sleeve 26 engages the adjoining face of the washer 30, the latter defining the "lower stop" for piston 40 travel.

Figure 2C:
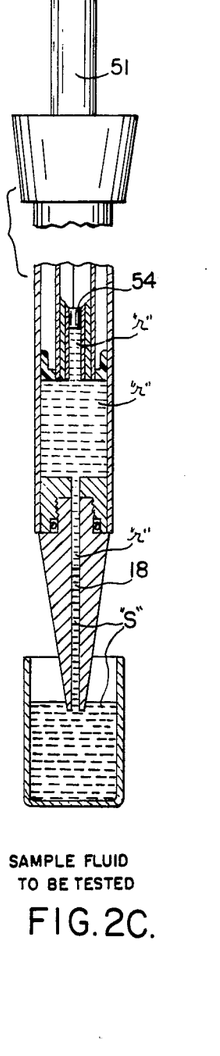
Figure 2D:
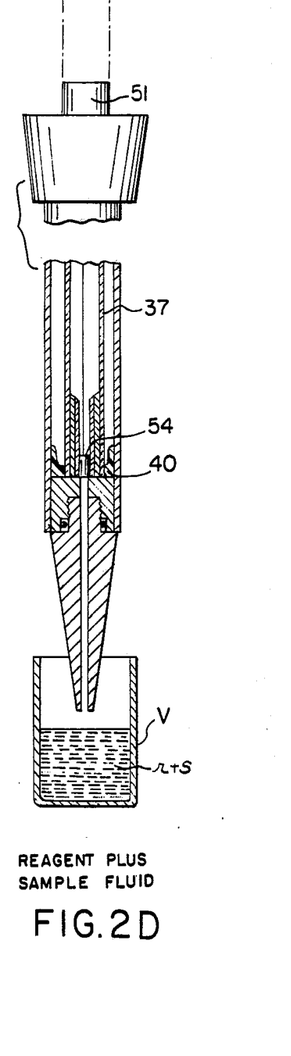

The construction of the piston and plunger assembly 35 may be preselected as will be understood to also provide for any desired piston 40 travel or stroke within tube 12 to thus define a preselected volume for fluid chamber A. In the embodiment disclosed herein it is intended that with the actuator 51 fully depressed whereby the sleeve member 26 bottoms against the washer 30 (lower stop), the piston 40 has moved completely through the main fluid chamber A and is abutting the upper wall 19 of the plug 13, thus defining zero volume in chamber A and thereby substantially completely expelling air and/or any fluid from said chamber. This position for piston 40 is illustrated in FIG. 2D.

With the actuator 51 held in its fully depressed condition and the piston 40 engaging the flat wall 19 of the plug 13, the pipette is ready to accept a suitable reagent and sample to be tested.

With the probe tip 16 immersed in a suitable reagent material as illustrated in FIG. 2, the thumb pressure on the actuator button 51 may be relieved sufficiently to cause the pressure exerted by the coil spring 43 to slidably move the complete plunger assembly 35 upwardly within the tube 12, as viewed in FIG. 1, whereby piston 40 creates an aspiration or suction within the fluid chamber A so as to draw the reagent material into said chamber. As the piston 40 moves upwardly to thus progressively increase the volume of the fluid chamber A the said chamber is maintained completely filled with reagent material as well as the bore 18 of the probe tip 16 and the bore 14 of the plug 13.

Depending upon the volume of reagent material desired to be used, said material continues to be drawn into the fluid chamber A until the top surface 26a of the sleeve member 26, as seen in FIG. 1, abuts against the overlying shoulder 25 on the cap member 20, said engagement thus defining the "upper stop" for piston 40 travel.

The proposed volume of fluid that can be accommodated in the fluid chamber A, as will be understood, is determined by the diameter of the piston 40 as well as the length of stroke thereof, the latter being determined by the distance between the top edge 26a of the sleeve member and the shoulder 25 of the cap member.

It is contemplated that the pipette of the present invention may accommodate a volumetric range of 0.005 milliliters to 3.0 milliliters. In the present embodiment of the pipette, a piston stroke of one-half inch has been employed and a piston 40 diameter of 11/32 inch to provide a volume capability of 0.7 milliliters.

With thumb pressure completely released from the actuator button 51, coil spring 53 is operative to force said actuator button, the attached rod member 50 and hence the piston 54 to slidably move upwardly through the precision bore glass tube 56 and create and aspiration or suction sufficient to draw reagent material into that portion of the said tube 56 between the bottom face of piston 54 and the lowermost edge of said tube as viewed in FIG. 1, which portion may be referred to as a "secondary chamber."

As aforementioned, the internal diameter of the glass tube 56 is exactly determined as well as the stroke of the glass tube 56 is exactly determined as well as the stroke of piston 54 to thereby provide the secondary fluid chamber with an exact predetermined volume. In the present structure, a volume of 0.005 milliliters has been utilized, but which may be selectively changed to accommodate any volume desired.

The upward movement of piston 54 continues until that top surface 51b of annular rim 51a of actuator button 51 abuts against the upper wall 23a of cap member 20. At this instant the fluid chamber A and the aforedefined "secondary chamber" are completely filled with reagent material as well as the bore 18, probe tip 16 and the plug bore 14. This position is illustrated in FIG. 2A.

The pipette is then raised to lift the probe tip out of the reagent fluid material but to remain over said material as illustrated in FIG. 2B, and thumb pressure is again applied to the actuator button 51 to move said actuator, rod member 50 and piston 54 downwardly in the direction of arrow C in FIG. 1 and against the pressure exerted by coil spring 53.

Since the modulus of coil spring 43 is greater than the modulus of coil spring 53, the sleeve member 26 reamins in its upper position as viewed in FIG. 1 during this interval of piston 54 movement. As a result, the volume of reagent material within the secondary chamber is expelled therefrom and into the fluid chamber A wherein it displaces a like volume of said reagent out of chamber A and through the connecting plug bore 14 and prove tip passageway 18 to atmosphere and back into the container K of reagent material, said displaced volume being represented by the droplet $d$ as illustrated in FIG. 2B.

With the actuator button 51 abutting the top surface 26a of sleeve member 26 the piston 54 has moved to the position as viewed in FIG. 2B whereby all of the reagent material has been expelled from the secondary chamber.

With the thumb pressure thus sustained the pipette may then be lifted out of the reagent fluid material, and if desired, the probe tip wiped clean of any of said material that may be clinging to the exterior surface, and then said probe tip is inserted into the sample fluid to be tested. This position is illustrated in FIG. 2C. Thumb pressure on the actuator button 51 may then be released to permit the piston 54 to be again moved upwardly within tube 56 as to create sufficient aspiration or suction and draw reagent material $r$ back into the "secondary chamber" while drawing a like volume of the sample fluid $s$ to be tested into the bore or passageway 18 of the probe tip 16, as also illustrated in FIG. 2C.

As will be understood, the dimensions of the probe tip 16 may be preselected so that all of the desired volume of sample fluid to be tested is accommodated within its bore or passageway 18 to thereby prevent it from admixing with the reagent material prior to expulsion from the pipette.

The pipette is then moved to a position over a suitable reaction vessel V as illustrated in FIG. 2D, and thumb pressure is again applied to the actuator button 51 in the direction of arrow C in FIG. 1 sufficiently to completely depress the same and cause the ejectment or expulsion of the sample fluid to be tested and the reagent material into the reaction vessel V where they are admixed $r+s$ prior to test.

As will be realized, the reagent material also functions during ejectment to rinse or flush the pipette of all residue reagent material and/or sample material to thus enable the pipette to be immediately used for subsequent tests of either the same or different samples to be tested and/or reagent materials to be used therewith. It may also be necessary on occasion to provide an additional rinse with water.

It will now also be realized that the pipette of the present invention is readily simple in operation, and is capable of carefully metering exact volumes of reagent materials and sample fluids to be tested. Further, with the novel differential spring characteristics of the piston and plunger assembly 35, i.e., between coil springs 43 and 53, the single actuator button 51 is capable of aspirating both the sample to be tested and reagent material into the pipette and thereafter operable to expel both fluids preparatory to testing.

It will also now be apparent that the pipette of the present invention is especially designed to enable a single sample of fluid, as for example a body fluid, to be readily analyzed under emergency or "STAT" conditions and which device carefully and efficiently meters out both the sample to be analyzed and the reagent material, and is operable to accurately control the amounts of said reagent and sample used in said device, therefore making it difficult to make an error and likewise eliminates the need to use highly skilled help.

Figure 3:
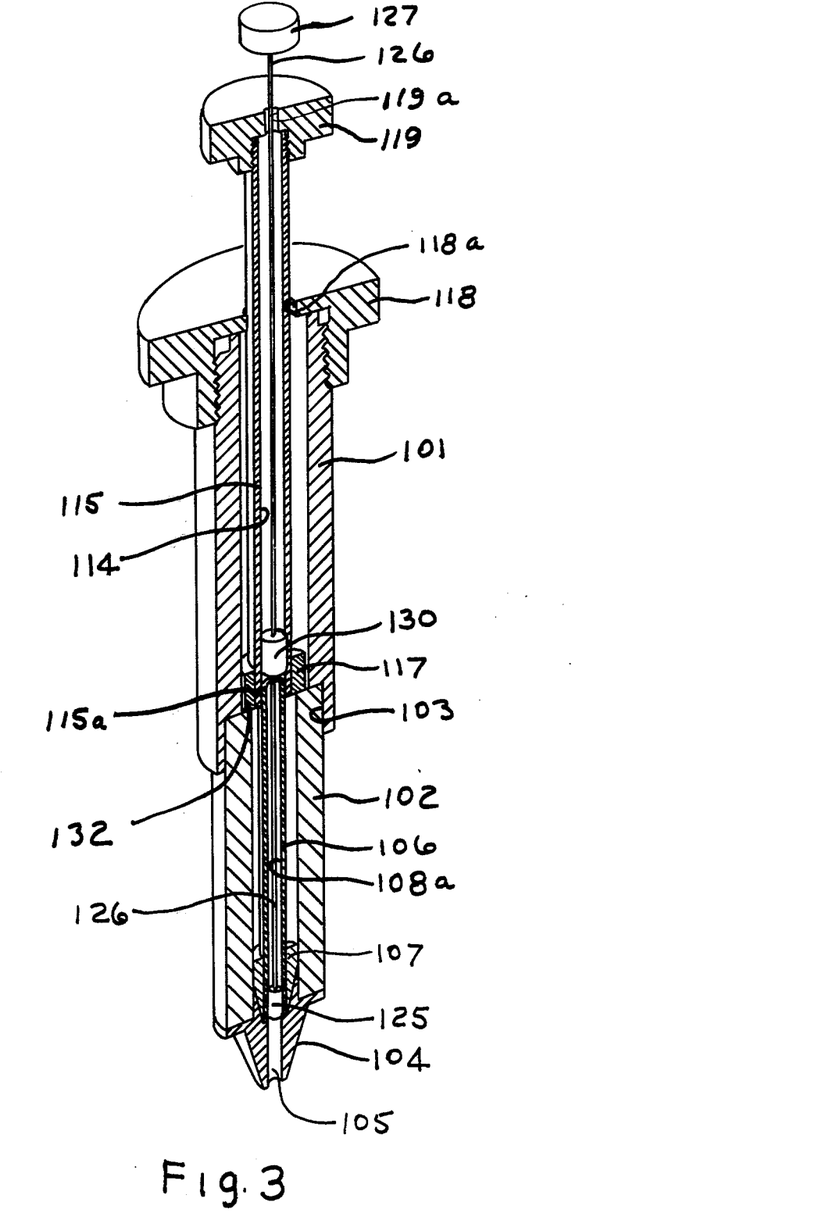
FIG. 3 is a vertical longitudinal sectional view of a second embodiment of pipette also herein referred to as the coaxial barrel pipette being shown in this view in its expelled condition.
Figure 4:
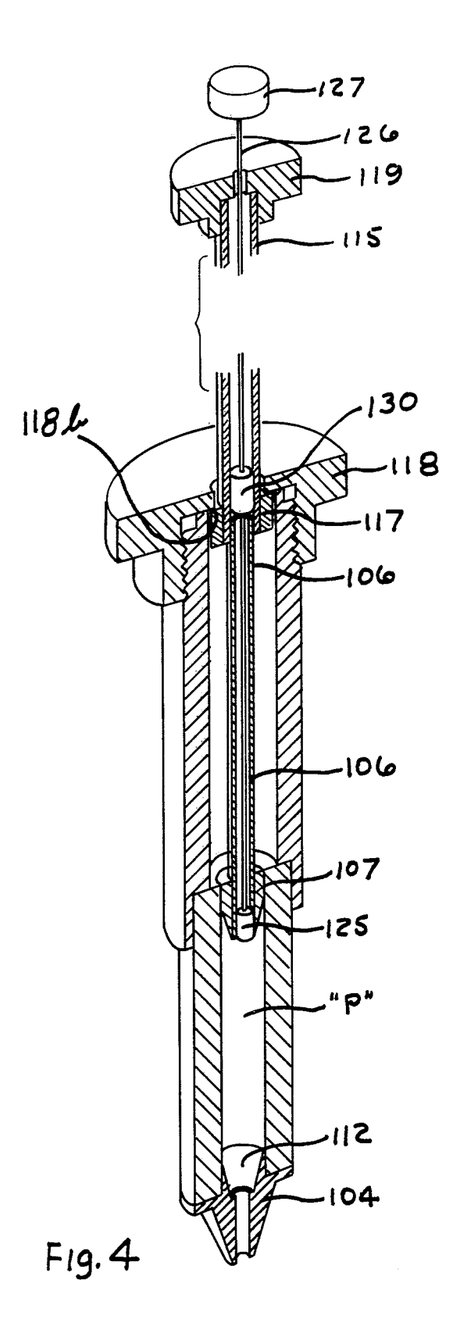
FIG. 4 is a view similar to FIG. 2 but with the inner barrel assembly shown in one of its actuated positions effective to draw fluid into the chamber of the outer barrel assembly.
Figure 5:
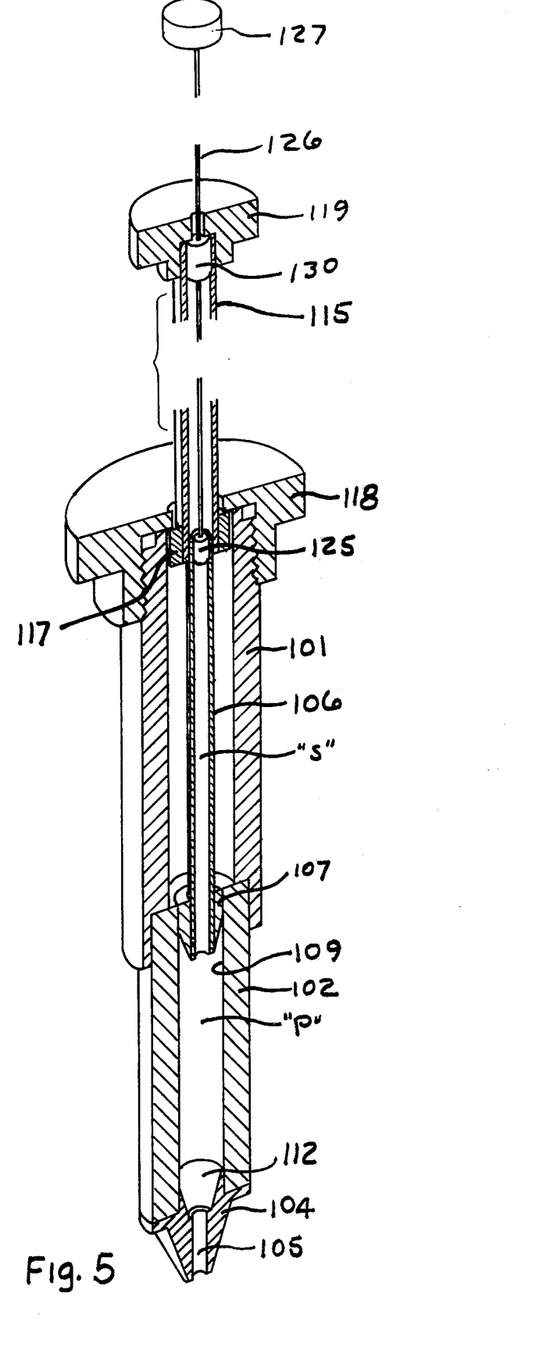
FIG. 5 is a view similar to FIGS. 2 and 3 but with the plunger and piston unit of the inner barrel assembly actuated to one of its positions effective to draw a volume of fluid into the chamber of the inner barrel assembly while simultaneously drawing a like volume of fluid into the probe tip of the outer barrel assembly.

In FIGS. 3-5 is illustrated a second embodiment of pipette device incorporating the present invention.

FIG. 3 shows the pipette in its "at rest" condition preparatory to its being used; FIG. 4 shows the primary plunger assembly in an actuated condition to aspirate or draw a suitable reagent material into the primary fluid chamber P, and FIG. 5 shows the secondary plunger further actuated to draw a volume of sample fluid to be tested into the probe tip of the pipette and simultaneously a like volume of reagent material into the secondary fluid chamber S.

With reference to FIG. 3, the pipette is seen to be generally cylindrical in overall configuration, being formed of a pair of tubular members 101, 102 which are disposed in longitudinal extension and securely fastened together by any suitable means such as an adhesive cement, tubular member 101 may preferably be formed of any suitable metallic material such as stainless steel whereas tubular member 102 may preferably be formed of glass material.

As shown tubular member 101 is provided with a recess 103 on its one end into which is fitted one end of tubular member 102. The dimensions of the said tubular members 101 and 102 are chosen to enable exact volumes of fluids to be accommodated therein.

The opposite end of tubular member 102 mounts a probe tip 104 which has a passageway 105 centrally therethrough communicating with the primary fluid chamber P.

A coaxial plunger assembly including a primary plunger assembly and a secondary plunger assembly is mounted within the pipette and is operable to draw and expel fluid material into and from the same.

For this purpose, as best seen in FIG. 3, the plunger assembly includes an elongated tube 106 having a piston 107 securely fastened to its lower end. Said piston is somewhat conical in configuration, and is of such diameter as to be in fluid-tight relation at is upper portion with the interior wall 109 of tubular member 102.

As seen in FIGS. 3 and 4, the contour of the piston 107 is such as to enable it to closely nest within a similarly shaped seat 112 formed on the upper portion of the probe tip 104 when the primary plunger assembly is moved to its fully depressed condition as depicted in FIG. 3 to thereby provide for the expulsion of all fluid from the primary fluid chamber P, the latter having therefore "zero volume" at that instant.

The opposite end of tube 106 is securely fastened at 115a to the internal wall 114 of tube 115 at its one end, as best seen in FIG. 3.

Tube 115, in turn, has it said one end 115a disposed centrally within and attached to plug member 117, said tube extending therefrom centrally upwardly through tube 101, as best seen in FIG. 3, through aperture 118a in cap member 118 which is threadedly mounted on the upper end of tube member 101. A suitable actuator knob 119 is mounted on the upper end of tube 115 and is intended to accommodate the manual application of pressure thereto sufficient to enable the tube 106 and attached piston 107 to be moved through tube 102.

With this primary plunger assembly, it is intended that upon application of manual force to the actuator knob 119 to raise the piston 107 upwardly through tube 102, from its FIG. 3 position to its FIG. 4 position, aspiration or suction of reagent material into the primary fluid chamber P is accomplished.

The secondary plunger assembly is carried coaxially within the primary plunger assembly and enables an exact or metered volume of sample fluid to be drawn into the pipette.

For this purpose, a generally cylindrical piston 125 is disposed within tube 106 and attached to one end of rod member 126, said rod member extending upwardly centrally through tube 115 and projecting outwardly through aperture 119a in actuator knob 119. The opposite end of said rod member 126 mounts an actuator button 127. A stabilizer cylinder 130 is mounted on rod member 126 intermediate its ends, and in the present construction is carried through tube 115 upon movement of rod member 126.

Piston 125 is in fluid-tight relationship with the internal wall 108a of tube 106, and is intended to be movable from its FIG. 3 position to its FIG. 5 position sufficiently as to aspirate or draw fluid into the secondary fluid chamber S then formed and defined between the bottom end of tube 106 and the bottom face of piston 125.

The positions occupied by the primary plunger assembly and secondary plunger assembly in their repetitive "at rest" condition are shown in FIG. 3.

The plug member 117 is shown seated upon annular seat 132, such position defining the "lower stop" for the primary plunger assembly whereat said instant, the piston 107 is also seated upon seat 112 of probe tip 104 which, as aforesaid, also defines "zero volume" for the primary fluid chamber P.

As best seen in FIG. 4, the primary plunger assembly has been moved to its uppermost position whereat the plug member 117 lies against the annular rim 118b of cap member 118, such position defining the "upper stop" for the primary plunger assembly.

As also illustrated in FIG. 4, the position of the plug member 117 in its "upper stop" position provides the maximum volume for the primary fluid chamber P. As will be apparent, the volume of said primary chamber P may be predetermined by preselecting the length of stroke and diameter of the primary piston 107 and associated elements.

The upper limit of movement of the secondary plunger assembly is illustrated in FIG. 5 whereat stabilizer cylinder 130 abuts the actuator button 119 at the upper end of tube 115 such position defining the "upper stop" for the secondary piston 125 thereby also defining the maximum volume for secondary chamber S.

The lowermost position or "lower stop" for secondary piston 125 is illustrated in FIG. 4 whereat the stabilizer cylinder 130 abuts the upper edge of tube 106 at which said position the bottom face of piston 125 is flush with the bottom edge of tube 106 thus defining "zero volume" in secondary fluid chamber S.

With this pipette construction, in use it is held in the hand of the user with the primary and secondary plunger assemblies in the position illustrated in FIG. 3. with the probe tip 104 immersed in reagent material, the actuator knob 119 is pulled upwardly as viewed in its FIG. 4 position to raise the piston 107 and aspirate or draw reagent material into the primary fluid chamber P.

The pipette is then lifted out of the reagent material, the probe tip wiped clean and then immersed into the sample fluid to be tested.

The actuator button 127 of the secondary plunger assembly is then pulled upwardly to its FIG. 5 position which is sufficient to draw reagent material into the secondary fluid chamber S while simultaneously drawing a like volume of sample fluid into the passageway 105 of the probe tip 104 and possibly into the lower end of the primary fluid chamber P as defined by the annular seat 112 of the probe tip 104.

The pipette is then lifted out of the sample fluid and placed over a suitable reaction vessel where the primary plunger assembly is first actuated through knob 119 to its FIG. 3 position effective to expel the sample fluid and reagent material from the primary fluid chamber P into the vessel. The secondary plunger assembly is then actuated by depressing the button 127 to its FIG. 3 position effective to expel the reagent material from the secondary fluid chamber S so as to rinse or flush the tube 106 and passageway 105 of the probe tip 104 of any residual fluid(s) and thus ready the pipette for subsequent test use.

FIGS. 6(A-D) illustrate a third embodiment of pipette of the present invention.

In this configuration, the primary piston identified at 150 is disk shaped and attached to the lower end of tube 152 which corresponds to tube 37 of the embodiment of FIG. 1.

The remaining elemental construction for the primary plunger assembly is the same as that disclosed in the aforesaid pipette structure of FIG. 1.

The secondary plunger assembly is also modified, and includes a rod member 160 formed of exact diameter of any suitable material, as for example stainless steel, and which has its one end securely fastened to the actuator button 51' corresponding to actuator button 51. The opposite end of rod member 160 is seen to project into an aperture 150a formed centrally in disk shaped piston 150.

The diameter of rod member 160 and that of the aperture 150a are such as to provide a slidable, fluid-tight relation between the surface of the rod member and the aperture wall. Rod member 160 replaces the rod member 50, piston 54 and the glass precision bore tube 56 in the initial pipette embodiment of FIG. 1. The differential spring action provided by coil springs 43 and 53 are retained in the present embodiment and operate in the same manner as in the embodiment of FIG. 1.

Figure 6A:
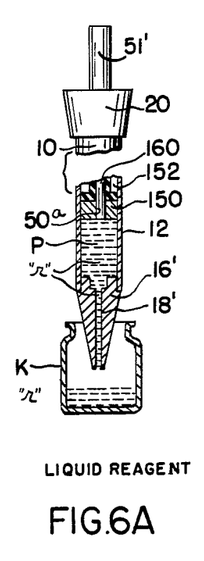
Figure 6B:
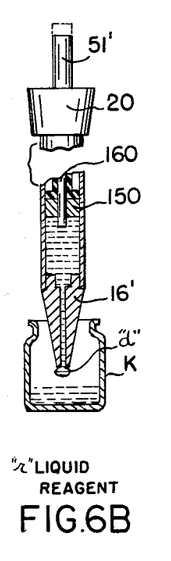
Figure 6C:
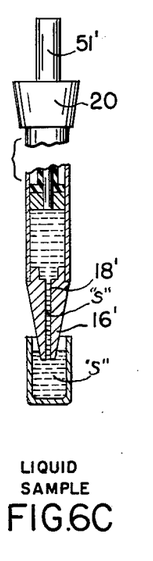
Figure 6D:
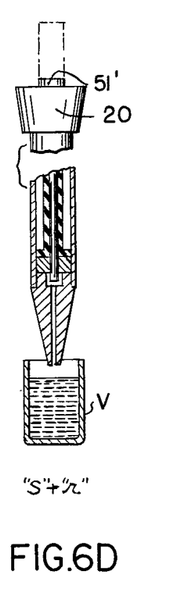

With this construction, and assuming the actuator button 51' is fully depressed as viewed in FIG. 6D, upon releasing the thumb pressure from the same, the primary piston 150 is raised upwardly within the pipette body to cause the aspiration or suction of reagent material r into the fluid chamber P. Piston 150 is raised to its uppermost position as illustrated in FIG. 6A, the fluid chamber P reaches its maximum volume and is completely full of reagent material as well as the bore 18' of the probe tip 16'.

With the pipette disposed over the reagent container K, the actuator button 51' is again depressed against the pressure of the coil spring 53 whereby the rod member 160 projects through aperture 150a of piston 150 and into the reagent material r in fluid chamber P. As illustrated in FIG. 6B the projection of rod member 160 into said chamber displaces a like volume of reagent material out through the bore 18' of the probe tip 16' as represented by droplet d.

With the actuator button 51' maintained in its FIG. 6B depressed condition, the probe tip of the pipette is placed into the container of sample fluid s to be tested, FIG. 6C, and the actuator button 51' is then released and permitted to return to its fully extended position illustrated in FIGS. 6C and 6A. With this release of actuator button 51', a predetermined volume of sample fluid s is aspirated or drawn into the bore 18' of the probe tip 16'. As will be understood, the aspirated volume of sample fluid will be equal or substantially equal to the displacement volume of that part of the rod member 160 which projects into the reagent material r in chamber P.

Thereafter, the pipette is disposed over a suitable reaction vessel V, as illustrated in FIG. 6D, and the actuator button 51' is fully depressed to force the sample fluid s and reagent material r into said vessel. And, as will be understood, in this manner the fluid chamber P and the bore 18' of probe tip 16' is rinsed clean of any traces of sample fluid to thereby ready the pipette for subsequent use.

What is claimed is:

1. A pipette device for providing analysis of single samples of liquids comprising an elongated body having a chamber for holding liquids therein, a probe tip on one end of said body and having a passageway defining the inlet and outlet for said chamber, a primary plunger assembly movable disposed in said chamber and actuatable to aspirate and expel liquids from said chamber, said primary plunger assembly being actuatable in a first direction into said chamber to define zero chamber volume and actuatable in a second direction to aspirate a predetermined volume of a first liquid material into said passageway of said probe tip and into said chamber to substantially fill said chamber, a second plunger assembly disposed within said body and actuatable in said first direction to expel a predetermined portion of said first liquid material from said chamber, said second plunger assembly being actuatable in said second direction to effect the aspiration of a second liquid into the inlet of said chamber, and said actuator being thereafter actuatable in said first direction to expel both said first and second liquids from said chamber.

2. A pipette device as is defined in claim 1 and wherein the primary and second plunger assemblies include means to actuate the same and expel the first and second fluid materials from said chamber and passageway.

3. A pipette device as is defined in claim 1 and wherein the second plunger assembly includes means for displacing a predetermined volume of the first fluid material from said chamber.

4. A pipette device as is defined in claim 3 and wherein the means for displacing the predetermined volume of first fluid material is subsequently actuatable to aspirate a second fluid material into the inlet of said chamber.

5. A pipette device as is defined in claim 4 and wherein the second plunger assembly is actuatable in a first direction to displace a predetermined volume of the first fluid material from said chamber and actuatable in a second direction to aspirate said second fluid material into said inlet.

6. A pipette device as is defined in claim 1 and wherein the second plunger assembly is disposed within the primary plunger assembly.

7. A pipette device as is defined in claim 6 and wherein the second plunger assembly is movable relative to said primary plunger assembly to effect a displacement of a predetermined volume of the first fluid material from the chamber.

8. A pipette device as is defined in claim 1 and wherein the primary plunger assembly includes piston means which defines the variable volume of the fluid chamber between it and the inlet passageway.

9. A pipette device as is defined in claim 1 and wherein the second plunger assembly includes piston means movable relative to the primary plunger assembly and operable to displace a predetermined volume of the first fluid material from the fluid chamber.

10. A pipette device as is defined in claim 9 and wherein the piston means of the second plunger assembly is projectable into the fluid chamber to effect the displacement therefrom of the predetermined volume of the first fluid material.

11. A pipette device as is defined in claim 1 and wherein resilient means are interposed between the primary plunger assembly and the second plunger assembly, being operable to urge said assemblies to a normal position within the body of said pipette.

12. A pipette device as is defined in claim 11 and wherein the resilient means includes a plurality of spring means.

13. A pipette device as is defined in claim 12 and wherein at least one of said plurality of spring means is in operative engagement with the primary plunger assembly and is operable to retain said primary plunger assembly in said normal position until a predetermined movement of the second plunger assembly has been attained.

14. A pipette device as is defined in claim 11 and wherein the resilient means comprising first spring means operatively interposed between the body and the primary plunger assembly and effective to urge said assembly to its normal position, and second spring means operatively interposed between the primary plunger assembly and the second plunger assembly and operable to urge said second plunger assembly to its normal position.

15. A pipette device as is defined in claim 14 and wherein the spring modulus of the first spring means is greater than the spring modulus of the second spring means.

16. A pipette device for providing analysis of single samples of liquids comprising an elongated body provided with a chamber for holding liquids therein, a probe tip on one end of said body and having a passageway defining the inlet and outlet for said chamber, a primary plunger assembly having piston means movably disposed in said chamber to aspirate and expel liquids from said chamber, tube means connected to said piston means, a second plunger assembly including piston means disposed in said tube means and movable therethrough, actuator means mounted on said body and extending exteriorly thereof, means interconnecting said actuator means and the piston means of said primary and second plunger assemblies, said actuator means being operable to cause the movement of the primary piston means in a first direction into said chamber to define zero chamber volume and thereafter actuatable in a second direction to aspirate a first liquid material into said chamber, said piston means of said second plunger assembly being thereafter movable by said actuator means in said first direction to cause the expulsion of a predetermined volume of said first liquid from said chamber and thereafter actuatable by said actuator means in said second direction to enable the aspriation of a like volume of a second liquid material into the inlet of said chamber, and said actuator being thereafter actuatable in said first direction to expel both said first and second liquids from said chamber.

17. In a pipette device as is defined in claim 16 and wherein the actuator means is operable to cause the projection of the piston means of the second plunger assembly into the fluid chamber effective to cause a corresponding volume displacement of the first fluid material therefrom.

18. In a pipette device as is defined in claim 16 and wherein the means interconnecting the actuator means and the piston means of the primary and second plunger assemblies includes a pair of spring means one of which is interposed between the body and the primary plunger assembly and the second being interposed between the primary plunger assembly and the second plunger assembly.

19. In a pipette device as is defined in claim 18 and wherein the modulus of the said one spring means is greater than the modulus of the second spring means.

20. A pipette device for providing analysis of single samples of liquids comprising, an elongated body having a chamber for holding liquids therein, a probe tip attached to one end of said body and having a passageway defining the inlet and outlet for said chamber, a primary plunger assembly comprising a disk-shaped piston disposed in said body defining one end of said chamber, a tube attached at its one end to said piston, said tube extending upwardly through said body, and its opposite end securely fastened to sleeve means movably disposed in said body, first spring means interposed between said sleeve means and said body effective to urge said piston to a normal position defining a maximum volume for said chamber, a second plunger assembly comprising a rod member extending through said tube and having means defining piston means on its one end, actuator means carried on said body and connected to the opposite end of said rod member, second spring means interposed between said sleeve means and said actuator means effective to urge said second plunger assembly to a normal at rest position within said tube member, said actuator means being operable to move the diskshaped piston to a position adjacent the probe tip to define zero volume in said chamber, said disk-shaped piston being thereafter movable by said first spring means to enable the aspiration of a first liquid material into said chamber, said actuator means being operable to affect the movement of the piston means of the second plunger assembly through the tube in a first direction and cause the expulsion of a predetermined volume of the first liquid material from said chamber, and said piston means being thereafter movable by the second spring means to enable the aspiration or a like volume of a second liquid material into the inlet of said chamber.

21. In a pipette device as is defined in claim 20 and wherein the movement of the actuator means in the first direction is effective to cause the piston means of the second plunger assembly to be projected into the fluid chamber and cause a displacement of a corresponding volume of the first fluid material from said chamber.

22. A pipette device for providing analysis of single samples of fluids comprising, an elongated body having a fluid chamber therein, a probe tip attached to one end of said body and having a passageway defining the inlet and outlet for said chamber, a primary plunger assembly comprising a first piston disposed in said body defining one end of said fluid chamber, a tube communicating with said chamber being attached at its one end to said piston, said tube extending upwardly through said body and its opposite end secure fastened to sleeve means movably disposed in said body, first actuator means operatively connected to said sleeve means, a second plunger assembly comprising a second piston disposed in said tube, a rod member disposed in said tube and attached at its one end to said second piston and extending through said tube, second actuator means carried on said body and connected to the opposite end of said rod member, said first and second actuator means being operable to move the first and second pistons to a position to define zero volume in said chamber, said first actuator means being thereafter operable to cause the movement of said first piston and enable the aspiration of a first fluid material into said chamber, said second actuator being thereafter operable to cause the movement of the second piston and enable the aspiration of said first fluid material into said tube and simultaneously therewith of a second fluid material into the inlet of said chamber.

23. A pipette device as is defined in claim 20 and wherein the second plunger assembly comprises an elongate rod attached at one end to the actuator means, and the other end of said rod defining piston means.

24. A pipette device as is defined in claim 20 and wherein the piston of the primary plunger assembly is formed centrally with an aperture into which the piston means of the second plunger assembly is movable.

25. A pipette device as defined in claim 24 and wherein the piston means of the second plunger assembly is in fluid-tight relation with the wall defining the aperture in the piston of the primary plunger assembly.

26. A pipette device as defined in claim 20 and wherein the second plunger assembly is movable relative to the primary plunger assembly to effect the displacement of the predetermined volume of the first liquid material from the chamber.

27. A pipette device as defined in claim 20 and wherein the spring modulus of the first spring means is greater than the spring modulus of the second spring means.

28. A pipette device as defined in claim 20 and wherein the elongated body includes a transparent tubular part having a predetermined diameter of accurate dimension defining the chamber which together with the primary plunger assembly provides for an accurate volumetric aspiration and expulsion of the first liquid.

29. A pipette device as defined in claim 28 and wherein the rod member of the second plunger assembly has a predetermined diameter of accurate dimension which together with the second plunger assembly provides for an accurate aspiration and expulsion of the second liquid.

30. A pipette device as defined in claim 28 and wherein primary fixed stop means are operable with the primary plunger assembly to provide accurate controlled travel of the primary plunger assembly.

31. A pipette device as defined in claim 30 and wherein the fixed stop means includes stop means disposed in spaced relation to each other in the body, and the sleeve means being movable with the primary plunger assembly to engage each said stop means.

32. A pipette device as defined in claim 29 and wherein secondary fixed stop means in said body are operable with said second plunger assembly to provide for an accurate expulsion and aspiration of the second liquid.

33. A pipette device as defined in claim 32 and wherein the secondary fixed stop means is formed on the sleeve means.

* * * * *